(12) United States Patent
Fiedler

(10) Patent No.: US 6,192,272 B1
(45) Date of Patent: Feb. 20, 2001

(54) IMPLANT

(75) Inventor: Dirk Fiedler, Ismaning (DE)

(73) Assignee: Implex Aktiengesellschaft Hearing Technology, Ismaning (DE)

( * ) Notice: Under 35 U.S.C. 154(b), the term of this patent shall be extended for 0 days.

(21) Appl. No.: 09/311,564

(22) Filed: May 14, 1999

(30) Foreign Application Priority Data

Aug. 20, 1998 (DE) .............................. 198 37 863

(51) Int. Cl.$^7$ .................................................. A61N 1/00
(52) U.S. Cl. .................................................. 607/2
(58) Field of Search .................. 607/2, 5, 9, 33, 607/34, 36, 63

(56) References Cited

U.S. PATENT DOCUMENTS 5,817,130 * 10/1998 Cox et al. ................................. 607/5
6,038,473 * 3/2000 Olson et al. ............................. 607/5

FOREIGN PATENT DOCUMENTS 26 22 245 12/1977 (DE) .
35 36 111 5/1986 (DE) .

OTHER PUBLICATIONS

Grundlagen der Akkutechnik, Funkschau, vol. 15, 1996, Jul. 3, 1996, pp. 37–41.

* cited by examiner

Primary Examiner—Scott M. Getzow
(74) Attorney, Agent, or Firm—Nixon Peabody LLP; David S. Safran

(57) ABSTRACT

An implant comprising an electric power consuming device electrically coupled to an electric power source including an anode, a cathode and at least one potential probe which is independent of the anode and the cathode. By providing at least one potential probe which is independent of the anode and the cathode, implants can be monitored and controlled to avoid process which can damage the electrodes and shorten the service life of the electrodes and the service life of the implant itself.

21 Claims, 3 Drawing Sheets

IMPLANT

BACKGROUND OF THE INVENTION

1. Field of the Invention

This invention relates to an implant including an electric power consuming device connected to an electric power source with an anode and a cathode. This invention also relates to such an implant which consumes electric power itself and/or which is coupled to a separate, implanted device which consumes electric power.

2. Description of Related Art

In currently available implants which require an electric power source for operation, for example, cardiac pacemakers, hearing aids, stimulation devices and the like, either primary cells or secondary cells are used as the electric power source. A drop in the efficiency of the electric power source which endangers implant operation can be prevented by replacing or recharging the cell before the expected service life of the electric power source expires. However, because any replacement of the electric power source requires surgery on the implant wearer, achieving a long service life of the electric power source is very important and is of the highest priority in the field of implant technology.

In order to be able to predict the efficiency of the electric power source provided in the implant, whether it be a primary or secondary source, and to also prevent processes that damage the individual electrodes which can occur especially in charging processes of an electric power source made as a secondary cell, the electrodes should be monitored with respect to certain characteristics such as current and voltage.

In an implant equipped with a conventional electric power source, the electrodes of the electric power source cannot be observed and monitored independently from the other electrode. Rather, the characteristics of current and voltage which can be measured outside the power source, are always referenced to the entire combination of the electrodes provided in the electric power source. When these characteristics are measured, they are generally dependent on the fact that these electrodes have predictable properties during discharge, at rest and optionally, during charging. However, this measurement can be adulterated by simultaneous processes which polarize the electrodes differently. Thus, this measurement allows conclusions regarding the instantaneous state of the electric power source only under current conditions and only with accurate knowledge of the simultaneous processes under the boundary conditions prevailing at the time.

For example, when charging a secondary electrochemical cell, the equilibrium potentials of the two active electrodes are shifted to more negative (negative electrode) and more positive (positive electrode) potentials due to the existing internal resistances. The internal resistances are thus composed of ohmic and non-ohmic portions. The ohmic portions generally relate to contact and electrolytic resistors. The non-ohmic portions are dictated by the electrode composition and geometry and the electrochemical processes which take place on the electrodes.

Overall, there is a very complex network of resistive, capacitive and inductive components which can no longer be broken down especially when there is loading, i.e. when the electric power source supplies the implant with electrical energy. Therefore, a simple current/voltage measurement cannot provide the basis for concluding which of the electrodes involved behaves as desired and which does not.

Only by extensive experience with a given system under clearly defined boundary conditions (for example, "discharging at C/2 rate to an end discharge voltage of 1.5 V"; "charging at C/10 rate for 14 h") can one skilled in the art assess whether the electric power source being tested is "good" or "bad" from simply measuring current and voltage values. In addition, even if the discharging behavior is known for a certain current load with a certain cut off criterion for a given electric power source, one skilled in the art still cannot exactly predict the behavior of the electric power source under different conditions, for example, at $\frac{1}{10}$ or $\frac{1}{100}$ of the current load at the known boundary conditions. At best, one skilled in the art can only give an estimate.

SUMMARY OF THE INVENTION

In view of the foregoing, the primary object of the present invention is to devise an implant which allows more accurate and more reliable measurement of the electrode characteristics.

Another object of the present invention is to devise an implant which allows more accurate and more reliable monitoring of the electrode characteristics.

These objects are achieved by providing an implant of the initially mentioned type in which the electric power source has at least one potential probe which is independent of an anode or a cathode. In this manner, a reference potential is provided which is independent of the anode and cathode of the electric power source and by which unwanted secondary reactions or undesirably intense secondary reactions on the electrodes under consideration can be detected and prevented by controlled monitoring and/or control of individual electrode potentials relative to the reference potential.

Thus, when the respective electrode properties are known, the electrodes can be prevented from being irreversibly damaged, which can lead to premature failure of the electric power source. In an implant in accordance with the present invention, it is no longer necessary to combine extensive technical knowledge based on years of experience with tedious series of tests as required in the present implant designs. Rather, with the present invention, definitive and generally valid conclusions are possible with respect to the pertinent electrodes after performing a few, relatively non-time critical, measurements. Processes which damage electrodes can thus be easily avoided without the need for an analysis of the entire respective current/voltage curves based on numerous assumptions. By practicing the present invention, longer service lives of the electrodes used in the electric power source will result and premature access to the implant which would require surgery on the implant wearer is thereby avoided.

More specifically, in one embodiment of the present invention, the electric power source may be an electrochemical power source or a super-capacitor. Such an electrochemical power source may be made as a galvanic element, especially as a primary element, secondary element or as a fuel cell. The electric power source of the implant can be provided with an electrically conductive housing which has a tap which is used as the potential probe. For reasons of production engineering, this embodiment is the simplest to build since a tap from the outside may be attached to the housing of the electric power source, for example, by soldering, without requiring penetration into the housing. In this embodiment, the housing can have several sections electrically insulated from one another, at least two of the housing sections having a tap which are used as potential probes. For example, the housing of the electric power source provided in the implant can have a first housing section which surrounds the anode and a second housing section which surrounds the cathode, the second housing section being electrically insulated relative to the first housing section and the first and the second housing section each having a tap used as potential probes. In this embodiment of the present invention, the taps serve another function in addition to providing reference potentials for measurements of the anode and the cathode in that the taps also provide information on the state of the interior of the electric power source of the implant on various areas within the housing of the electric power source.

In yet another embodiment of the present invention, a third housing section may be provided between the first housing section and the second housing section which is electrically insulated relative to the first and the second housing sections. The first, second, and third housing sections may each include a tap which are used as potential probes. These potential probes allow the measurement of the potentials of the respective housing sections. Thus, information about the state of the individual areas of the electric power source of the implant can be thereby obtained. Of course, the present invention may also be modified for use in housings which are electrically insulated relative to the housing interior such that the housing is electrically neutral to the outside.

In another preferred embodiment of the present invention, there may also be provided, at least one more electrode which may be used as a potential probe for measuring the potential difference between an electrolyte and the anode or the cathode.

The implant may also be provided with a telemetry means in order to transmit data between the implant and an external measurement and/or control device. The telemetry means in which data signals are transmitted by magnetic induction or via infrared transmission are known in the prior art and are already being used in numerous implants.

These and other objects, features and advantages of the present invention will become more apparent from the following detailed description of the preferred embodiments when viewed in conjunction with the attached drawings.

DETAILED DESCRIPTION OF THE INVENTION

Figure 1:
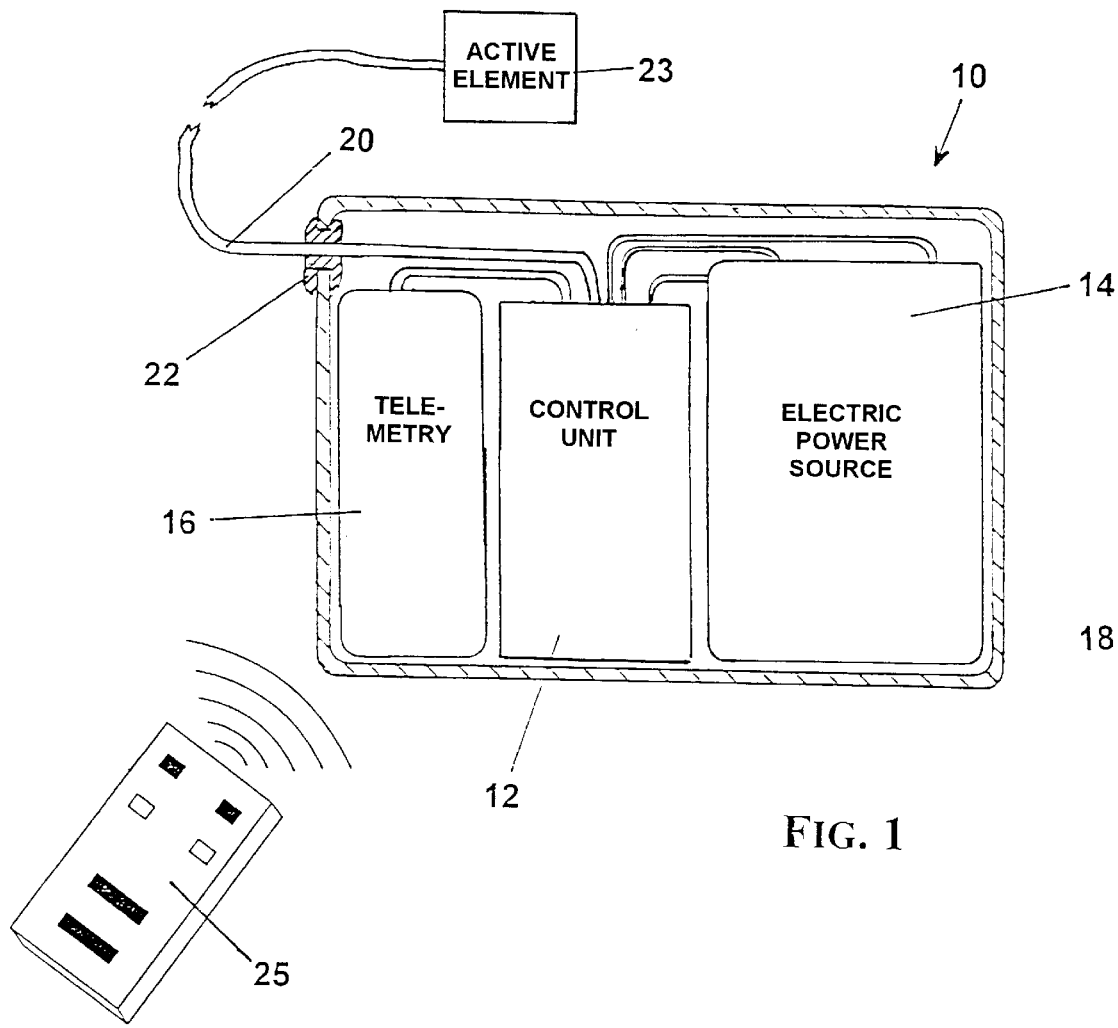
FIG. 1 shows a schematic sectional view of an implant in accordance with the present invention.

As illustrated in FIG. 1, the implant 10 has a control unit 12, an electric power source 14 and a telemetry means 16 which are all accommodated in a common implant housing 18 and which are connected to one another by appropriate wires. Furthermore, the control unit 12 is connected to wire 20 which is routed out of the implant housing 18 through an opening 22 and leads to an active element 23 which executes the desired implant function. For example, the active element 23 can be an actuator of a fully implanted hearing aid, stimulation electrodes, drug dispensing devices, or the like. The implant can receive via the telemetry means 16 interrogation signals or control signals from an external measurement and/or control device 25 and cab transmit data signals to the control device 25. If the electric power source 14 is a rechargeable power source, the telemetry means 16 may also be used for receiving current signals sent from the control device 25 for recharging of the electric power source 16.

Figure 2:
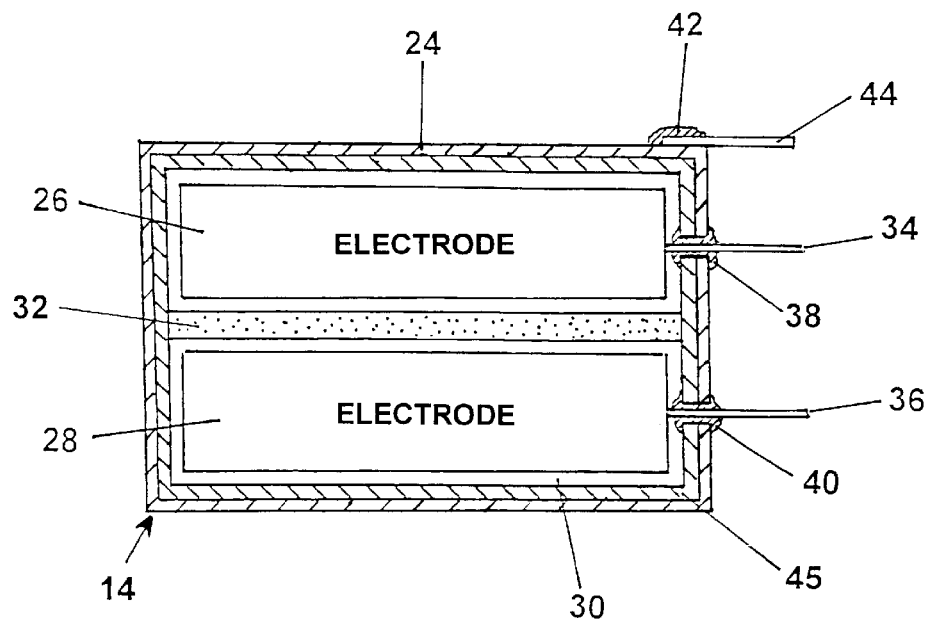
FIGS. 2 through 6 each show a sectional view of a respective embodiment of an electric power source in accordance with different embodiments of the present invention which may be used in the implant of FIG. 1.

FIG. 2 illustrates the details of an electric power source 14 in accordance with one embodiment of the present invention as applied to the implant 10 described above. In this embodiment, the electric power source 14 includes two electrodes 26 and 28 located in an electrically conductive, preferably hermetically sealed housing 24 which is made, for example, of metal. Although it is irrelevant for the operation of the implant described here which of the two electrodes 26 and 28 is the anode and which the cathode, for reasons of simplicity in this description, the electrode 26 is referred to as the anode 26 and the electrode 28 is referred to as the cathode 28. The interior of the housing 24 may be filled with an electrolyte 30 and the anode 26 and the cathode 28 are separated from one another by a diaphragm 32. The diaphragm 32 is an electrical insulator, but allows ion migration between the two electrodes 26 and 28. In this embodiment, the diaphragm 32 may be made as a microporous plastic separator. The anode 26 and cathode 28 are electrically insulated relative to the electrically conductive housing 24, for example, by means of an insulating layer 45 applied to the inside of the housing wall. Furthermore, the anode 26 and the cathode 28 are connected to the control unit 12 via wires 34 and 36 respectively, which, in turn, are routed through penetrations 38 and 40, respectively, out of the housing 24 as shown in FIG. 1. On the housing 24, there is a tap 42 on which a reference potential can be measured. If the housing is metal, the tap 42 can be made as a wire probe 44 which is conductively connected to the outside of the housing 24, for example, by soldering, as is illustrated in FIG. 2. In the illustrated embodiment, the housing is potential-free so that a zero potential can be tapped on the wire probe 44 as a reference to the potential of anode 26 and the potential of cathode 28.

It should be understood that the electric power source 14 in the present application is used as a general term encompassing all types of commonly used power sources. For example, the electric power source 14 may be an electrochemical power source or a primary electrochemical cell which uses any of the ordinary electrode/electrolyte systems. For example, $Zn/AgO$, $Zn/MnO_2$, lithium-based cells, organic systems, and those with liquid low-viscosity or high-viscosity electrolytes and solid electrolyte systems may all be used. Alternatively, if the electric power source 14 is made as a secondary electrochemical cell, metal/air batteries can be used, such as zinc/air systems, $Zn/MnO_2$ systems, nickel-cadmium cells, nickel/metal hydride systems, or lithium cells. In the present application, the term lithium cells is used in reference to cells in which a solid state cathode of interstitial compounds together with an anode of metallic lithium is used in combination with a liquid, organic electrolyte or electrolyte of a solid polymer or other solid or liquid electrolyte, as well as to lithium-ion cells with a liquid or solid polymer electrolyte, lithium alloy cells and the like.

If a polymer or solid electrolyte is used as the electrolyte, the polymer or solid electrolyte will perform a separator function in addition to its function as an ion conductor. Thus, in this situation, the diaphragm 32 shown in FIG. 2 can be eliminated. These polymer or solid electrolytes can be present in the form of true polymer or solid electrolytes or in the form of a microporous polymer with the electrolyte solution placed in its pores, or in the form of a gelled or solution-absorbing polymer or solid electrolyte.

In the "three-electrode device" shown in FIG. 2, the current-carrying electrodes 26 and 28 can be observed independently of one another by measuring and comparing the potentials on wire 34 and probe 44 an on wire 36 and probe 44.

Figure 3:
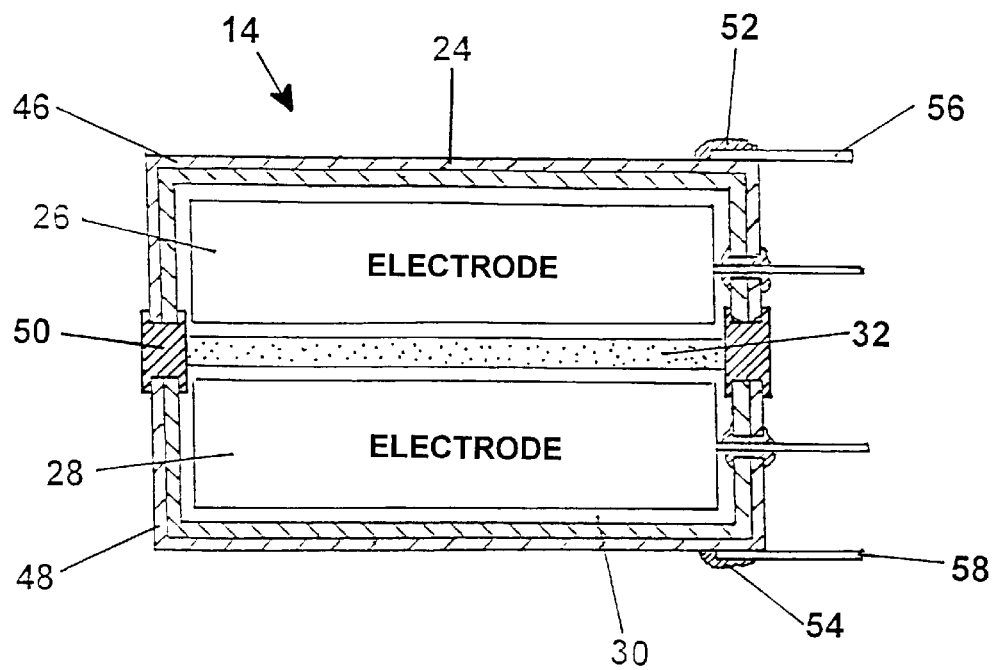

An alternative embodiment of an electric power source 14 in accordance with the present invention used in the implant 10 is illustrated in FIG. 3 and includes several potential probes which can be used depending on the measurement requirement. In this embodiment, the electrically conductive housing 24 is divided into two housing sections 46 and 48 which surround the electrodes 26 and 28 respectively. The electrodes 26 and 28 are located in an electrolyte 30 and are separated from one another by a diaphragm 32. An insulator 50 is provided between the housing sections 46 and 48. Taps 52 and 54 are provided on the housing sections 46 and 48 respectively so that the potential of the respective housing sections 46 and 48 can be measured via wires 56 or 58 in order to provide a reference potential in the evaluation of the electric power source 14.

Figure 4:
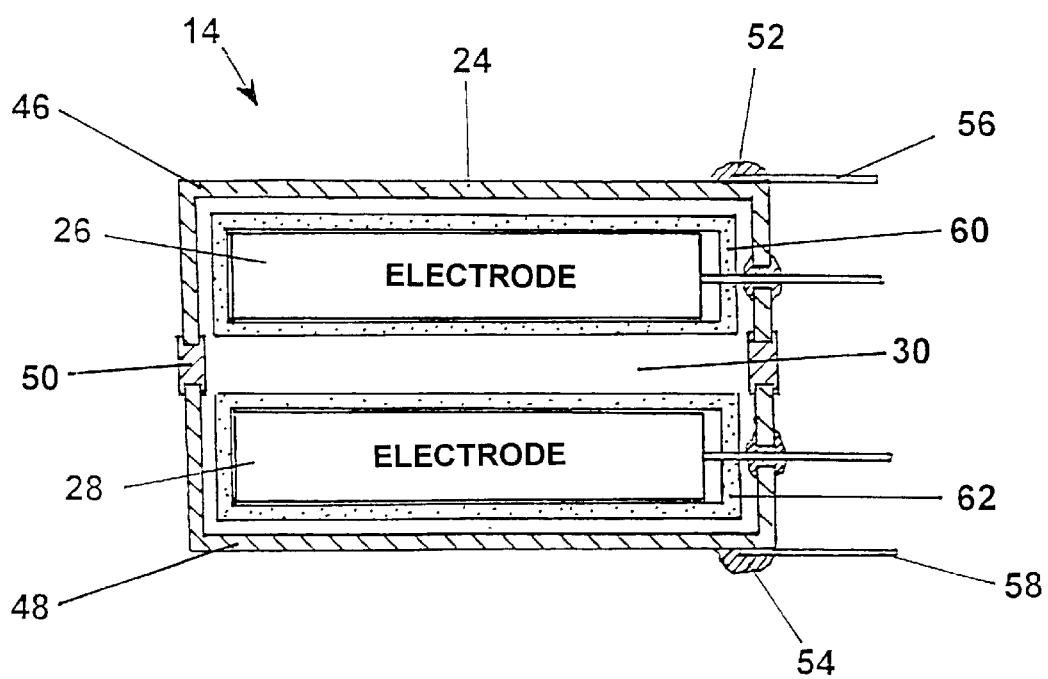

Instead of using a diaphragm 32 as shown in FIG. 3 to divide the housing interior into two areas which house the electrodes, the anode 26 and the cathode 28 of the electric power source 14 may each be surrounded by a diaphragm 60 and 62 respectively as illustrated in an alternative embodiment of FIG. 4. This design allows ion migration to and from the anode or the cathode, but also acts as an electrical insulator thereby preventing electron migration. If the housing 24 of the electric power source 14 is made of metal or another conductive material, the housing 24 may then be divided by a peripheral insulator 50 into two housing sections 46 and 48 thereby preventing a short circuit between the anode or the cathode and the housing.

Figure 5:
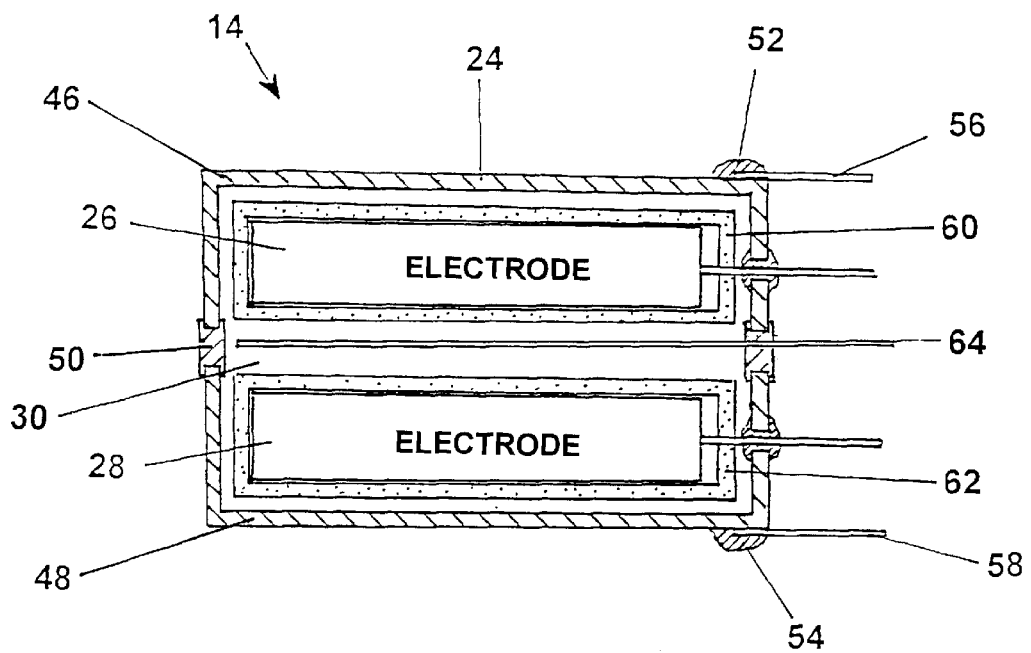

An alternative embodiment of the present invention is illustrated in FIG. 5 including an electric power source 14 equipped with three potential probes independent of the anode 26 and the cathode 28. Two of these potential probes are formed by wires 56 and 58 which are attached to taps 52 and 54 respectively and provide a means for measuring the potentials of the housing sections 46 and 48. The third potential probe 64 is located in the electrolyte 30 between the two electrodes 26 and 28. If the housing 24 is a conductive housing, provisions must be made for insulating the third potential probe 64 and the housing 24. As shown in FIG. 5, the third potential probe 64 can be routed through the housing 24 anywhere as long as provisions are made for suitable insulation. For example, a penetration through an electrically conductive housing can be provided by the component to be insulated such as through the feed line of the potential probe or by one of the wires which lead to the electrodes 26 and 28, these wires passing through the electric insulator in the opening of the housing. Furthermore two or more of these lines can be combined in a common penetration instead of having each of the lines routed out of the housing 24 through its own penetration.

Figure 6:
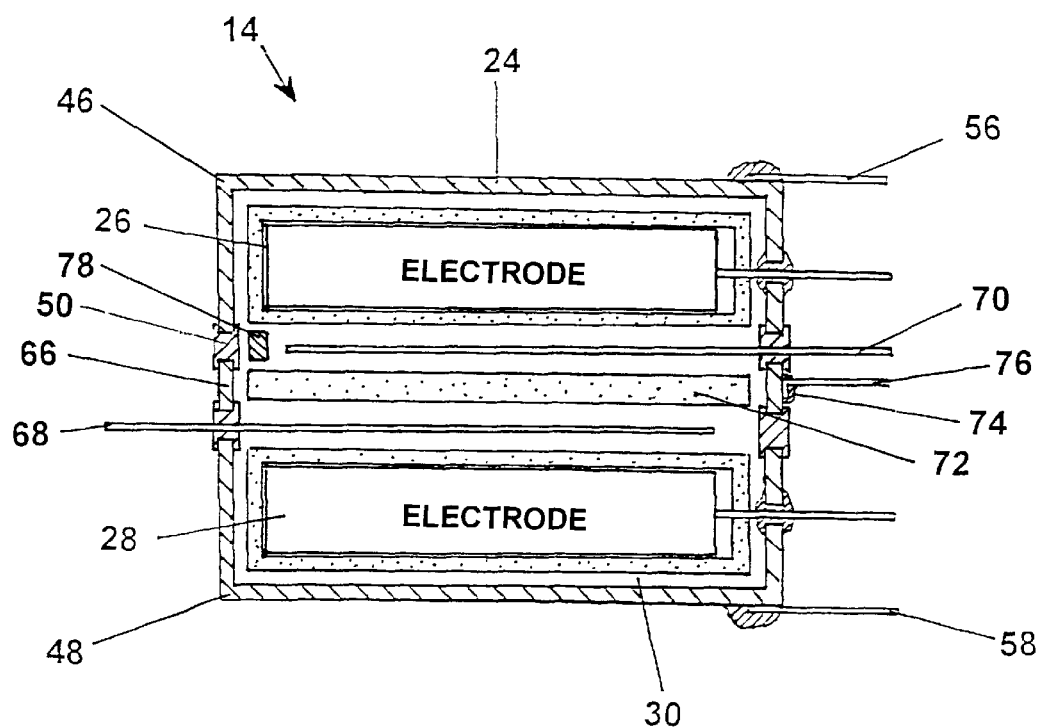

FIG. 6 shows another embodiment of an electric power source 14 as is used in the implant 10 described here. The housing 24 here is divided into three housing sections, a first housing section 46 which surrounds the anode 26, a second housing section 48 which surrounds the cathode 28, and a third housing section 66 located between the first and second housing sections 46 and 48. Provided between each of the housing sections is an insulator 50. In the space between the anode 26 and the cathode 28, there are two potential probes 68 and 70 which are electrically insulated from one another by a diaphragm 72. If the housing 24 is electrically conductive, the potential probes 68 and 70 can be routed through the insulators 50 in order to provide for insulation between the potential probes and the housing 24 in a manner analogous to the embodiment shown in FIG. 5. In addition, in the present embodiment electric power source 14 shown in FIG. 6, the third housing section 66 may also be provided with a tap 74 on which the potential of the third housing section 66 can be measured via wire 76.

It goes without saying that the embodiments described above may be combined with one another in various ways if provisions are made for suitable electrical insulation between the individual electrically conductive components, especially the electrodes, the potential probes and optionally, the housing. Thus, FIG. 6 shows an insulator 78 for shielding the potential probe 70 against the electrically conductive housing 24. An insulator of this type is not actually needed in the embodiment shown in FIG. 6 since its function is already being performed by the insulating connecting piece 50 located between the first and the third housing section. However, such an insulator 78 would be necessary if the potential probe is inserted at a point where no such insulator has been already integrated into the wall of housing 24.

Since the measurement probes are provided at the time of production in the above described implants, the measurement probes will be available for use long before the normally scheduled use. Thus, check measurements can be taken to monitor the implant and depending on the technology used in the implant, may provide an opportunity for improvements to the implant. Check measurements can be simple measurements of the potential differences between the reference electrode and an active electrode. However, more complex measurement processes may be carried out with the above described embodiments of the electric power source by using commercially available measurement equipment. For example, (cyclo)voltammetric studies with DC or combined DC/AC excitation signals and impedance spectroscopic measurements as well as other general electroanalytical methods commonly known in the art may be carried out depending on the objectives of the study or test. These measurements can also be carried out during the production of the electric power source 14 and be taken to monitor stability and utility until the implant is used.

In addition to these benefits prior to actual use, detectable electrode potentials acquire special importance and benefits during use of the implant. For example, it now becomes possible to interrupt the discharging process when the electrode enters an undesirable or harmful potential region by monitoring the behavior of the electrode. Subsequent processes can then be initiated to address the particular circumstance. Likewise, charging of the electric power source can also be interrupted in a controlled manner if one electrode enters an undesirable or even harmful potential region. It should be emphasized once again that this type of measurement and monitoring is not readily feasible in conventional two-electrode devices. And without these types of measurement and monitoring, information regarding the electric power source cannot be deemed reliable, thereby (giving rise to the possibility of irreversibly damaging the electric power source and adversely effecting the total service life of the implant.

From the foregoing, it should be apparent how the present invention provides an implant including an electric power source with at least one potential probe which is independent of the anode and the cathode. This allows one or more potential measurements in addition to the measurement of the electrode potentials for determining and monitoring of the condition of the electric power source. It should also be evident how the present invention may also be implemented with super-capacitors, especially with double layer capacitors, redox capacitors or pseudo-capacitors, and with fuel cells as noted previously.

While various embodiments in accordance with the present invention have been shown and described, it is to be understood that the invention is not limited thereto, and may be changed, modified and further applied by those skilled in the art. Therefore, this invention is not limited to the details shown and described previously but also includes all such changes and modifications which are encompassed by the appended claims.

What is claimed is:

1. Implant comprising an electric power consuming device and an electric power source including an anode and a cathode, said electric power source being electrically coupled to said electric power consuming device, wherein said electric power source includes at least one potential probe which is independent of said anode and said cathode.

2. Implant of claim 1, wherein said electric power source is an electro-chemical power source.

3. Implant of claim 2, wherein said electrochemical power source is a galvanic element.

4. Implant of claim 2, wherein said electrochemical power source is a fuel cell.

5. Implant of claim 1, wherein said electric power source is a super-capacitor.

6. Implant of claim 1, wherein said at least one potential probe is provided with a tap on an electrically conductive housing of said electric power source.

7. Implant of claim 6, further comprising a telemetry means for transmitting data between said implant and at least one of an external measurement device and an external control device.

8. Implant of claim 6, wherein said housing has a plurality of housing sections electrically which are insulated from one another; and wherein said at least one potential probe is provided with a tap on each of at least two of said plurality of housing sections.

9. Implant of claim 8, wherein said housing includes a first housing section which surrounds said anode and a second housing section which surrounds said cathode, said second housing section being electrically insulated relative to said first housing section; and wherein said at least one potential probe is provided with a tap on each of said first and said second housing sections.

10. Implant of claim 9, wherein a third housing section is provided between said first housing section and said second housing section, said third housing section being electrically insulated relative to said first and said second housing sections; and wherein said at least one potential probe is provided with a tap on said third housing section.

11. Implant of claim 10, further comprising a telemetry means for transmitting data between said implant and at least one of an external measurement device and an external control device.

12. Implant of claim 6, wherein said housing has an electrically conductive wall which is electrically insulated relative to an interior space of said housing.

13. Implant of claim 12, wherein said housing has a plurality of housing sections which are electrically insulated from one another; and wherein said at least one potential probe is provided with a tap on each of at least two of said plurality of housing sections.

14. Implant of claim 13, wherein said housing includes a first housing section which surrounds said anode and a second housing section which surrounds said cathode, said second housing section being electrically insulated relative to said first housing section; and wherein said at least one potential probe is provided with a tap on each of said first and said second housing sections.

15. Implant of claim 14, wherein a third housing section is provided between said first housing section and said second housing section, said third housing section being electrically insulated relative to said first and said second housing sections; and wherein said at least one potential probe is provided with a tap on said third housing section.

16. Implant of claim 15, further comprising a telemetry means for transmitting data between said implant and at least one of an external measurement device and an external control device.

17. Implant of claim 6, wherein said at least one potential probe further comprises at least one additional electrode for measuring potential of an electrolyte located between said anode and said cathode; and wherein said electric power source includes a galvanic element.

18. Implant of claim 17, wherein said housing has a plurality of housing sections which are electrically insulated from one another; and wherein said at least one potential probe is provided with a tap on each of at least two of said plurality of housing sections.

19. Implant of claim 18, wherein said housing includes a first housing section which surrounds said anode and a second housing section which surrounds said cathode, said second housing section being electrically insulated relative to said first housing section; and wherein said at least one potential probe is provided with a tap on each of said first and said second housing sections.

20. Implant of claim 19, wherein a third housing section is provided between said first housing section and said second housing section, said third housing section being electrically insulated relative to said first and said second housing sections; and wherein said at least one potential probe is provided with a tap on said third housing section.

21. Implant of claim 1, further comprising a telemetry means for transmitting data between said implant and at least one of an external measurement device and an external control device.

* * * * *